United States Patent [19]

Lewis et al.

[11] Patent Number: 4,847,209

[45] Date of Patent: Jul. 11, 1989

[54] LATEX AGGLUTINATION IMMUNOASSAY IN THE PRESENCE OF HEMOGLOBIN

[75] Inventors: Lynette A. Lewis, Goshen; Lowry Messenger, Granger; Frances M. Yeager, Middlebury; Kin F. Yip, Elkhart, all of Ind.

[73] Assignee: Miles Inc., Elkhart, Ind.

[21] Appl. No.: 118,469

[22] Filed: Nov. 9, 1987

[51] Int. Cl.$^4$ .................. G01N 33/546; G01N 33/72
[52] U.S. Cl. ........................ 436/533; 422/61; 436/67; 436/534; 436/808; 436/825; 436/826
[58] Field of Search .............. 436/533, 534, 825, 67, 436/826, 808; 422/61

[56] References Cited

U.S. PATENT DOCUMENTS

| | | | |
|---|---|---|---|
| 4,362,531 | 12/1982 | de Steenwinkel | 436/825 X |
| 4,536,478 | 8/1985 | Sokoloff | 436/825 X |
| 4,600,698 | 7/1986 | Toth | 436/825 X |
| 4,629,692 | 12/1986 | Dean | 436/67 X |

OTHER PUBLICATIONS

Gribnau et al, "Particle-Labelled Immunoassays: A Review", J. Chromatog. 376 (1986) 175–189.

Hechemy et al, "Latex Particle Assays in Laboratory Medicine. Part I", Lab. Management, 22 (1984) 27–40.
Hechemy et al, "Latex Particle Assays in Laboratory Medicine. Part II", Lab. Management, 22 (1984) 26, 29–35.
Masson et al, "Particle counting immunoassay- an overview", J. Pharm. Biomed. Anal., 5 (1987) 113–117.
Goldstein et al, "Glycated Hemoglobin: Methodologies and Clinical Applications", Clin. Chem., 32 (1986) B64–B70.

Primary Examiner—Christine M. Nucker
Attorney, Agent, or Firm—Andrew L. Klawitter

[57] ABSTRACT

A latex agglutination immunoassay method for determining an analyte in a blood sample in which the pH of the reaction mixture is maintained at about 8.5 or greater in order to overcome nonspecific agglutination of latex particles by hemoglobin present in the sample. The method is particularly applicable to the determination of glycated hemoglobin, e.g., Hb Alc. In another embodiment, native hemoglobin (Ao) can be determined based on its ability to cause agglutination of latex particles suspended in an aqueous solution having a pH of about 8 or below.

31 Claims, 4 Drawing Sheets

LATEX AGGLUTINATION IMMUNOASSAY IN THE PRESENCE OF HEMOGLOBIN

BACKGROUND OF THE INVENTION

This invention relates to methods for determining an analyte in a blood sample based on latex agglutination immunoassay. More particularly, the invention concerns a method for overcoming nonspecific agglutination from hemoglobin present in a test sample. The invention is particularly directed to the determination of glycated hemoglobin, e.g., hemoglobin A1c, in samples of whole blood.

Latex agglutination immunoassay is based on the formation of detectable agglutination by binding between a multivalent latex antibody reagent and a corresponding multivalent form of the antigen or hapten. Where an analyte of interest is itself multivalent relative to the latex antibody reagent, a direct assay can be conducted. However, where the analyte of interest is not multivalent, such as in the case of a low molecular weight hapten, a competitive assay is performed in order to quantitate such haptenic analyte. An agglutinator reagent is added to the system comprised of a plurality of epitopic binding sites for the anti-analyte antibody reagent. Binding between the agglutinator reagent and the latex antibody reagent results in formation of detectable agglutination. With increasing amounts of analyte, which competes with the agglutination reagent for binding to the latex antibody reagent, the amount of resulting agglutination is reduced.

The prior art has applied the latex agglutination immunoassay method principally to serum or plasma samples in order to determine analytes of interest in blood. It has been found that the presence of whole blood components can give rise to nonspecific agglutination of the latex reagent. Therefore, in situations where it is desirable or necessary to assay whole blood, the precision of the assay result is subject to possible large errors. This particularly applies to the determination of blood components associated with erythrocytes such as hemoglobin derivatives of diagnostic importance, e.g., the glycated hemoglobins.

SUMMARY OF THE INVENTION

It has now been found that nonspecific agglutination in latex agglutination immunoassays conducted on whole blood samples can be effectively overcome by maintaining the pH of the reaction mixture at about 8.5 or above. It is believed that nonspecific agglutination is due to the presence of native, unmodified hemoglobin, referred to as hemoglobin Ao, which, because of its net positively charged character, is attracted nonspecifically to negatively charged latex particles. By performing the assay at elevated pH, the hemoglobin Ao net charge would be neutralized and agglutination by electrostatic attraction to the latex particles would not occur.

Accordingly, the present invention applies to the determination of an analyte in a blood sample by latex agglutination immunoassay wherein (a) an aqueous reaction mixture is formed by combining the blood sample with a multivalent latex antibody reagent comprising an anti-analyte antibody, or a fragment thereof, bound to a water suspensible latex particle, and additionally when the analyte is only monovalent, with an agglutinator reagent comprising a plurality of epitopic binding sites for the anti-analyte antibody or fragment thereof, and (b) the resulting agglutination in the aqueous reaction mixture is measured as a function of analyte in the blood sample. The invention is applicable to the use of latex particles, e.g., polystyrene latex, which have an effective net negative surface charge when suspended in an aqueous solution having a pH of about 7 or below.

The observed nonspecific agglutination of the latex particles by hemoglobin also provides the basis for determining hemoglobin Ao in a blood sample. A reaction mixture is formed comprising the blood sample and suspended latex particles and the pH maintained at about 8 or below. The resulting agglutination is a function of hemoglobin Ao in the sample. At pH 8 or below, the latex particles retain their net negative surface charge and are agglutinated by electrostatic attraction of hemoglobin.

BRIEF DESCRIPTION OF THE DRAWINGS

FIG. 1 is a graph showing the effect of varying hemoglobin Ao (native, unmodified hemoglobin) concentrations on the agglutination of latex particles.

FIG. 2 is a graph showing the effect of pH on the ability of hemoglobin Ao to agglutinate latex particles.

FIG. 3 is a graph showing the correlation between HbA1c assay results obtained following the present invention and results obtained following a standard affinity chromatography method.

FIG. 4 is a graph showing a hemoglobin Ao dose response curve following the method of the present invention.

DESCRIPTION OF THE PREFERRED EMBODIMENTS

Figure 1:
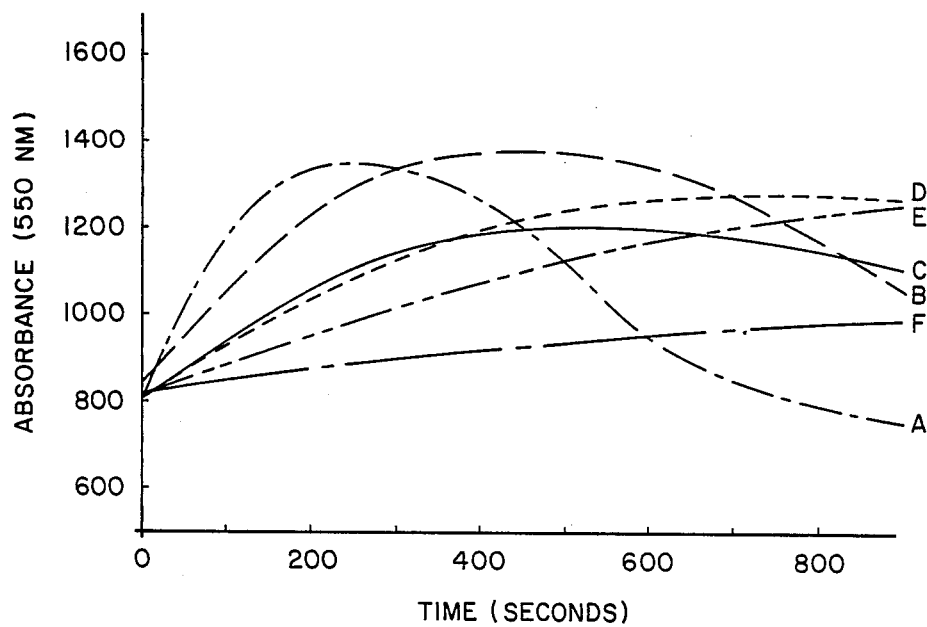
FIGS. 1-4 are graphical representations of data collected according to the experiments described in the Examples below.

In the course of developing a latex agglutination immunoassay for determining the hemoglobin derivative known as hemoglobin A1c, it was found that the dose response curve was essentially the same between assays run at pH 7.4 with the complete reagent system and those run in the absence of the agglutination reagent. Latex coated with bovine serum albumin rather than the hemoglobin A1c analog was found also to be agglutinated in the presence of a blood sample. It was suspected that native hemoglobin in the blood sample could be the culprit. Treatment of the blood sample with the proteolytic enzyme pepsin eliminated the nonspecific agglutination. The multivalency of hemoglobin Ao, native hemoglobin that is unmodified at the N-terminal amino group in the beta-chain, would be destroyed by pepsin digestion. Furthermore, in subsequent experiments it was found that hemoglobin Ao agglutinates the latex particles in proportion to its concentration in an aqueous latex suspension.

It is therefore theorized, but is not considered critical to the present invention, that hemoglobin Ao interacts with the latex by ionic attraction between negatively charged groups on the surface of the latex, e.g., sulfate groups on polystyrene, and the positively charged amino groups on hemoglobin, e.g., the N-terminal amino groups on the beta-chain of hemoglobin. The tetrameric form of hemoglobin thereby affords sufficient multiple positive charges to cause agglutination by the bridging of latex particles. Further, it is believed that hemoglobin derivatives such as glycated hemoglobins are modified in a way that the positive charges are diminished or removed, so that a differential capacity to agglutinate latex particles exists between hemoglobin Ao and particular hemoglobin derivatives. Thus, it is possible to perform an assay for a particular hemoglobin derivative, e.g., hemoglobin Alc, which does not substantially cause nonspecific latex agglutination by conducting the assay under pH conditions that neutralize the nonspecific agglutination effect of hemoglobin Ao.

The present invention is applicable to agglutination immunoassays based on a variety of latex particles. Most latexes are composed of particles having a net negative surface charge at neutral pH. The charge repulsion between the negative surface charges on the latex is important in maintaining the particles in suspension. As used herein, the term latex is intended to mean the property of suspension of discrete microparticles in an aqueous liquid.

Latex particles useful in the present invention will be evident to the worker familiar with the field of latex agglutination immunoassay. In general, such particles require the properties necessary to serve as a stable support for the desired antibody reagent for the assay and to undergo agglutination in the presence of an agglutinator reagent sufficient for analytical purposes. Latex particles are prepared generally by emulsion polymerization or suspension polymerization [Bangs, L.B. (1984) Uniform Latex Particles, Seragen Diagnostics Inc., Indianapolis, Ind., USA]. Swollen emulsion polymerization can also be used [Ugelstad, J. et al (1980) Adv. Colloid and Interface Sci. 13:101-140]. A good selection of latex particles are commercially available. Polystyrene particles are particularly useful.

The density of the latex particles, without limitation, will vary generally between about 0.1 mg/mL and about 0.1 g/mL. Most latexes are composed of particles that are roughly microspherical, having diameters, without limitation, that vary between about 0.04 and about 1.2 microns.

The attachment of the antibody reagent to the latex particles is a matter of applying conventional techniques. In general, the attachment can be covalent or noncovalent. The antibody reagent can consist of whole antibodies, antibody fragments, polyfunctional antibody ? [aggregates, and the like. Normally, whole antibody or IgG fragments such as Fab, Fab', or F(ab')$_2$ are employed. The antibody reagent can be derived by any available technique such as conventional antiserum and monoclonal techniques.

Normally, conducting the immunoassay reaction at a pH of about 8.5 or greater will be sufficient to neutralize the positive character of hemoglobin Ao and thereby eliminate the nonspecific agglutination of the latex reagent in the presence of the blood sample. The pH of the reaction mixture will, of course, not be allowed to reach the point at which the immunoreactivity between the analyte and the latex reagent is substantially diminished, that is, to the point that a useful assay is no longer obtainable. Preferably, the pH of the aqueous reaction mixture will have a pH of between about 8.75 and about 10, preferably less than about 9.5, with a pH around 9.0 being particularly useful. Suitable buffers for this purpose can be selected on the basis of convenience and assay performance. Glycine and bicine buffers are preferred.

The agglutinator compound will be prepared according to techniques familiar to the field of agglutination immunoassays. This reagent will, in general terms, comprise a plurality of epitopic binding sites for the anti-analyte antibody reagent. Such sites can be provided by using the analyte itself or a suitable analog that retains sufficient capacity to be bound by the antibody for purposes of an assay. Such analog can, in the case of a protein analyte, comprise a suitable fragment, prepared synthetically or by digestion, comprising the epitope for the antibody reagent, e.g., glycated peptide residues of hemoglobin Alc as described in the examples below.

The present invention is applicable to the assay of test samples which comprise hemoglobin as a potential nonspecific interferant. Such test samples will generally comprise a lysate of a blood sample such as whole blood or separated erythrocytes.

The ability of hemoglobin Ao to agglutinate latex particles also provides a method for Ao determinations. In this embodiment, the latex particles need not carry an antibody reagent, nor is an agglutinator compound required. Simply by maintaining the pH of an aqueous mixture of hemoglobin and latex particles at about 8 or below, one can obtain agglutination correlatable with hemoglobin Ao concentration. The lower point of the useful pH range for this aspect of the invention will be the pH at which hemoglobin Ao is found empirically to lose its ability to agglutinate the latex particles. Normally, this will require a pH above about 4.

The present invention will now be illustrated, but is not intended to be limited, by the following examples.

EXAMPLES

1. PREPARATION OF REAGENTS

A. Antibody-Latex Reagent:

Materials Required:

2% latex suspension [0.085$\mu$ diameter polystyrene latex, Seragen, Indianapolis, Ind., U.S.A.]

Antibody solution [Monoclonal antibody prepared as described in U.S. Pat. No. 4,647,654, purified from ascites fluid by protein A affinity chromatography (BioRad Laboratories, Richmond, Calif., U.S.A.)]

10 mM glycine buffer, 0.02% azide, pH 9.3

100 mM NaCl

The antibody coating is done at a latex concentration of 0.5% and the antibody is normally used in a final concentration of 1 mg/mL in the coating reaction. An antibody solution at 2x concentration is prepared by diluting the required amount of antibody into a 10 mM glycine buffer with added NaCl to give the final conductivity desired (between 0.5 and 1.8 mohm). The 2% latex is diluted to 2x concentration (or 1%) by mixing with an equal volume of the 10 mM glycine buffer. The reaction is initiated by pouring the latex suspension into a vessel containing the antibody solution. The antibody solution is mixed with a magnetic stir bar when the latex is added. All solutions are at room temperature. The mixing is continued overnight (at least 15 hours) taking care to insulate the vessel so that heating from the magnetic stir plate does not occur. This can be accomplished by suspending the vessel above the stir plate leaving about an inch air space for insulation.

After the 15 hours mixing, the resulting suspension is divided equally into polypropylene centrifuge tubes (approximately 10 mL per tube) for a Sorvall SS-34 rotor [Dupont, Wilmington, Del., U.S.A.]. The suspension is centrifuged at 15,000 rpm (2700 x g) for 60 minutes. The supernatant is decanted. The pellet is washed two times with 10 mM glycine buffer containing the desired overcoating protein [typically 1% protease free bovine serum albumin (BSA-pf) obtained from Miles Inc., Elkhart, Ind., U.S.A.]. To wash the pellet, a volume of wash solution equal to the original volume in the tube is added. The pellet is resuspended by vigorous vortexing and short-term sonication (10–15 seconds at a time). After the initial resuspension, the Ab-latex is allowed to stand at room temperature for one hour before recentrifuging. After the initial resuspension and centrifuging, subsequent resuspensions are centrifuged immediately once the pellet is completely dispersed. After the second wash, the pellets are resuspended in a volume equal to the initial reaction volume. The suspension is filtered through a $0.8\mu$ filter and stored at 5° C.

The concentration is determined by measuring the absorbance at 546 nm of the original supernatant, the supernatant from the first and second washings, and a 100x dilution of the final sample. The sum of these absorbances is assumed to be 100% or equal to 0.5% latex. The absorbance of the final sample is divided by the sum of the absorbances used to calculate 100%. The absorbance of the 100x dilution of the final sample is multiplied by 100 to generate an absorbance for the final sample.

EXAMPLE

| Sample | $A_{546}$ |
|---|---|
| Supernatant | 0.044 |
| First Wash | 0.034 |
| Second Wash | 0.021 |
| Final (100 × dil) | 0.051 × 100 = 5.1 |
| 100% (or 0.5% latex) = 5.10 + 0.044 + 0.034 + 0.021 = 5.199 | |
| Latex concentration of final sample = (5.1/5.199) × 0.5% = 0.49% | |

B. Agglutinator Reagent:

Poly(aspartic acid) was prepared according to the procedure of Alpert J. Chromatography 266:23(1983).

Aminoethanol (80 mmoles) and 4,9-dioxa-1,12-dodecanediamine (20 mmoles) were dissolved in dimethylformamide (DMF) under argon. The solution was treated with a solution of poly(aspartic acid) (10 mmoles) and DMF. The reaction was stirred at room temperature for 1 hour and then 70° C. for 2 hours. The mixture was then cooled and most of the liquid was removed by evaporation under reduced pressure. The oily residue was washed repeatedly with ether and then warm tetrahydrofuran. The product was solidified and recovered by filtration. The crude product was dissolved in water and the pH was adjusted to neutral. The solution was then purified with a BioRad P6-DG desalting gel column (BioRad Laboratories, Richmond, Calif., U.S.A.). Fractions containing the amino-functionalized polymer were pooled and lyophilized.

The number of amino groups on the polymer was determined by Habeeb's TNBS assay [Anal. Biochem. 4:328-336(1966)] and found to be 22 per mg polymer.

Amino functionalized poly(aspartic acid) (10.7 mg) and SMCC (30 mg) were dissolved in DMF. The reaction was allowed to stir at room temperature for 2 hours. Ice water was added to the mixture and the activated polymer was separated from the mixture with a BioRad 6P-DG gel column. The activated polymer was then allowed to react at room temperature for 3 minutes with the glycated peptide (20 mg)

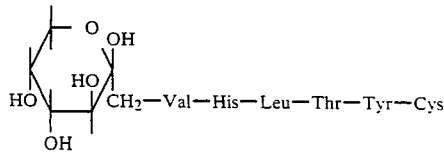

prepared according to the methods described in European Patent Publication No. 185,870. After the reaction, the product was again purified with a 6P-DG gel column and lyophilized.

The number of maleimido groups on the activated polymers was determined by the PDS assay [Grassetti and Murray, Arch. Biochem. Biophys. 119:44–49(1967)] and found to be 0.46 $\mu$mole per mg polymer. The amount of Glc-peptide on the polymers was determined by UV/Vis absorption measurement using the molar extinction coefficient at 275 nm for tyrosine and found also to be 0.46 $\mu$mole per mg polymer.

C. Bovine Serum Albumin-Coated Latex:

A 2% latex solution (4 ml) was mixed with the 10 mM glycine buffer containing 1% protease-free BSA (12 ml). The mixture was briefly sonicated.

2. INTERACTION OF THE BSA-COATED LATEX WITH HEMOGLOBIN Ao

I. At pH=7.4

The BSA-coated latex was diluted to a concentration of 0.036% in a 50 mM sodium phosphate buffer, 0.05% BSA, 0.02% sodium azide (pH=7.4). The latex was mixed with denatured blood samples having various known Ao concentrations. The change in absorbance at 550 nm at room temperature was recorded over time and is shown in FIG. 1 of the drawings [Hemoglobin Ao concentrations: A=99.5%, B=96%, C=90%, D=86%, E=78%, and F=71%].

II. At pH=9.0

The experiment was repeated using BSA-coated latex diluted to 0.05% in 50 mM glycine, 80 mM sodium chloride, 0.05% BSA, 0.02% sodium azide (pH=9.0). No agglutination was observed upon addition of any of the blood samples.

3. EFFECT OF pH ON HEMOGLOBIN Ao AGGLUTINATION

Figure 2:
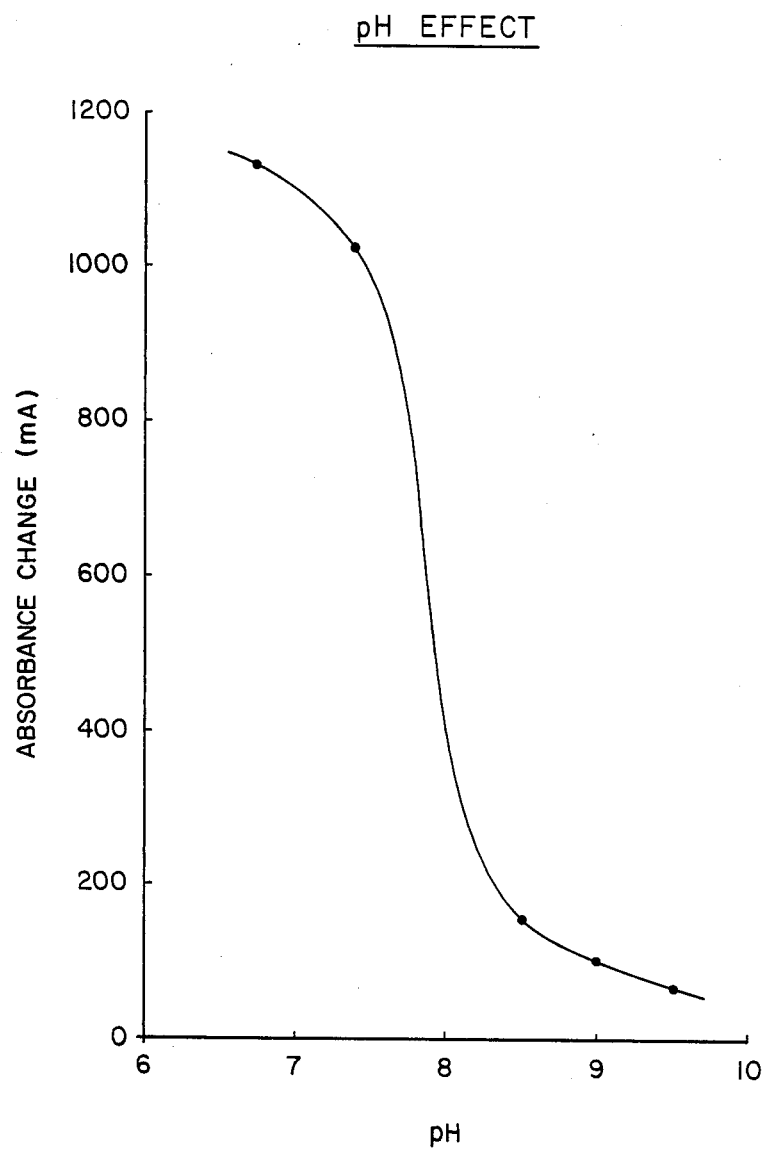

BSA-coated latex was diluted to about 0.03% with the assay buffer. A 0.5 ml volume of the diluted latex was mixed with denatured Ao and the reactions incubated at room temperature for 20 minutes. The absorption at 540 nm for each mixture was then measured. The results are shown in FIG. 2 of the drawings.

Hemoglobin Ao was present at about 16 g/dl before dilution with the denaturant solution. For pH=6.75 and 7.40, the buffer was phosphate at 50 mM and 80 mM sodium chloride. For pH=8.5, 9.0 and 9.5, the buffer was glycine at 50 mM and 80 mM sodium chloride.

4. ASSAY PROCEDURE FOR DETERMINATION OF % HbAlc

A. Reagents:

Ab-Latex

The concentrated Ab-Latex is diluted to the appropriate concentration with 200 mM glycine buffer, pH containing 0.05% BSA-pf and 0.1% sodium azide. Mannitol at a 4% concentration may also be present in the buffer. Following dilution, the Ab-latex solution is sonicated briefly (5 to 10 sec.)

Agglutinator

A working solution of the agglutinator reagent is prepared from 1.0 mg/mL water stock solution. A 10 μg/mL solution is prepared by diluting the stock with 20 mM phosphate buffer, pH 6, containing 0.1% BSA-pf and 0.1% sodium azide.

Blood-based Calibrators and Clinical Samples

Blood based calibrator and blood samples must be denatured before use. For use in the assay, blood samples are well mixed by a rocker mixer such as the Ames Aliquot mixer (Miles Inc., Elkhart, Ind., U.S.A.). These samples are then diluted 1:31 with denaturant/oxidant (3 M $NH_4SCN$, 2 mg/mL $K_3Fe(CN)_6$, 10 mM Tris, pH 7.5). The presence of the ferricyanide in the denaturant allows the diluted sample or calibrator to be used for the determination of the hemoglobin concentration. The samples are allowed to sit at least 15 seconds before assaying on the OPTIMATET$^{TM}$ Instrument (Miles Inc., Elkhart, Ind., U.S.A.) to allow for complete denaturation of the protein and oxidation of the heme.

B. Turbidimetric Assay for HbAlc

Three different procedures for the OPTIMATE instrument have been used for determination of HbAlc. Two are endpoint formats; one requiring the manual addition of the agglutinator solution and the other completely automating the assay. The third assay format is a rate assay. The following description briefly explains the general format of the three assays.

Endpoint Assay With Manual Addition of Agglutinator

1. Using Chemistry 37 - Program New Test, the following assay parameters are programmed as USER CHEMISTRY #25.
   Units - None
   Test Type - Endpoint
   Decimal Places - 2
   Dispenser Usage - A
   Lag Time A - 1200 sec. (the time between dispensing of reagents and absorbance read)
   Equil Time - 6 sec. (the time sample is held in the cuvette before absorbance read)
   Read Time - 5 sec. (time over which data is collected, absorbance is read 7.7 sec.)
   Cuvette Temp - 25° C.
   Standard Conc. - None
   Factor - 1000 (factor by which result is multiplied, converts to milliabsorbance units)
   Low I/A (Abs) - 2.000 (setting both the low and high absorbance limits to 2.00 forces the
   High I/A (Abs) - 2.000 OPTIMATE to print the actual absorbance readings for each sample)
   Low Normal - None
   High Normal - None
   Absorbance Filter - 540 nm
   Transport Temp - Room Temperature
   Sample Volume - 10 μL
   Reagent Volume - 0.5 mL 2 Prior to starting the assay, verify that the pipetter/diluter is equipped with a 100 μL sample syringe and a 1.0 mL reagent syringe. The turrets of the pipetter/diluter are set to 10% (10 μL) for the sample syringe and 50% (0.5 mL) for the reagent syringe.

3. Pipette at least 50 μL of sample into the OPTIMATE sample cups.

4. Prime the pipetter/diluter with the Ab-latex solution.

5. Manually dispense 25 μL of the agglutinator solution in the OPTIMATE reaction cups using an Eppendorf Repeater Pipette (1.25 mL capacity tip, setting =1). Leave blank cup #60 and any other cups in which the turbidimetric reaction is not to take place. Pipette 25 μL of buffer (20 mM phosphate, pH 6, 0.1% BSA-pf, 0.1% sodium azide) into these cups.

6. Start Chemistry #25 - USER CHEMISTRY #25 following all printed instructions. The OPTIMATE then automatically pipettes and dispenses sample and Ab-latex into the reaction cups and reads the absorbance after 20 minutes.

Endpoint Assay With Automatic Addition of Agglutinator

1. Equip the OPTIMATE with a Gilford Automatic Dispenser with 1.0 mL syringe. The communication cable is connected to port J4 on the back of the OPTIMATE. The use of this external dispenser is enabled by:
   a. Enter Utility 15 followed by the security code 980456.
   b. Enter Utility 50, Check =0, Option
   The turret of this dispenser is set to 50% (0.5mL).

2. Using Chemistry 37 - Program New Test, the following assay parameters are programmed as USER CHEMISTRY #24.
   Units - None
   Test Type - Endpoint
   Decimal places - 2
   Dispenser Usage - A and B
   Dispense B from Tower - Yes
   Time from Dispense A to Dispense B - 5 sec
   Lag Time A - 1200 sec
   Equil Time - 6 sec
   Read Time - 5 sec
   Cuvette Temp - 25° C.
   Standard Conc. - None
   Factor - 1000
   Low I/A (Abs) - 2.000
   High I/A (Abs) - 2.000
   Low Normal - None
   High Normal - None
   Absorbance Filter - 540 nm
   Transport Temp - room temperature
   Sample Volume - 10 μL
   Reagent Volume - 0.1 mL 3. Prior to starting the assay, verify that the pipetter/diluter is equipped with a 100 μL sample syringe and a 250 μL reagent syringe. The turrets of the pipetter/diluter are set to 10% (10 μL) for the sample syringe and 10% (25 μL) for the reagent syringe. Also verify that an immunoassay probe is used on the pipetter/diluter.

4. Pipette at least 50 μL of sample into the OPTIMATE sample cups.

5. Prime the pipetter/diluter with the agglutinator solution.

6. Prime the external dispenser with Ab-latex solution.

7. Start Chemistry #24 - USER CHEMISTRY #24 following all printed instructions. The OPTIMATE then automatically pipettes and dispenses sample and agglutinator into the reaction cups, followed by the addition of Ab-latex five seconds later. The absorbance of the reaction is read after 20 minutes.

Rate Assay

1. Equip the OPTIMATE with a Gilford Automatic Dispenser with a 1.0 mL syringe. The communication cable is connected to port J4 on the back of the OPTIMATE. The use of this external dispenser is enabled by:
   a. Enter Utility 15 followed by the security code 980456.

b. Enter Utility 50, Check =0, Option 20. The turret of the dispenser is set to 50% (0.5 mL).

2. Using Chemistry 37 - Program New Test, the following assay parameters are programmed as USER CHEMISTRY #23.

Units - None
Test Type - kinetic enzyme
Decimal Places - 2
Dispenser Usage - A and B
Dispense B from Tower - Yes
Time from Disp A to Disp B - 5 sec
Lag Time A - 20 sec
Equil Time - 5 sec
Read Time - 30 sec
Cuvette Temp. - 30° C.
Standard Conc - None
Factor - 1000
Low I/A (Abs) - 2.000
High I/A (Abs) - 2.000
Absorbance Filter - 540 nm
Transport Temp - 30° C.
Sample Volume - 10μL
Reagent Volume - 0.1 mL 3. Prior to starting the assay, verify that the pipetter/diluter is equipped with a 100 μL sample syringe and a 250 μL reagent syringe. The turrets of the pipetter/diluter are set to 10% (10 μL) for the sample syringe and 10% (25 μL) for the reagent syringe. Also verify that an immunoassay probe is used on the pipetter/diluter.

4. Pipette at least 50 μL of sample into the OPTIMATE sample cups.

5. Prime the pipetter/diluter with the agglutinator solution.

6. Prime the external dispenser with Ab-latex solution.

7. Start Chemistry #23 - USER CHEMISTRY #23 following all printer instructions. The OPTIMATE then automatically pipettes and dispenses sample and agglutinator into the reaction cups, followed by the addition of Ab-latex five seconds later. The absorbance of this reaction is read after the 14-second lag period. The absorbance is read for a total of 30 seconds. The OPTIMATE determines the linear regression line through the data it has collected and presents the data in terms of the change in absorbance per minute.

Hemoglobin Determination

For all blood samples, the concentration of hemoglobin in the sample must be determined in order to calculate the percent of HbA1c in the sample. The same denatured sample used for the determination of HbA1c is used for the hemoglobin determination using the following protocol.

1. Using Chemistry 37 - Program New Test, the following assay parameters are programmed as USER CHEMISTRY #26.

Units - None
Test Type - Endpoint
Decimal Places - 2
Dispenser Usage - A
Lag Time A - 300 sec
Equil Time - 6 sec
Read Time - 5 sec
Cuvette Temp. - 25° C.
Standard Conc - None
Factor - 1000
Low I/A (Abs) - 2.000
High I/A (Abs) - 2.000
Low Normal - None
High Normal - None
Absorbance Filter - 540 nm
Transport Temp - Room Temperature
Sample Volume - 70μL
Reagent Volume - 0.5 mL 2. Prior to starting the assay, verify that the pipetter/diluter is equipped with a 100μL sample syringe and a 1.0 mL reagent syringe. The turrets of the pipetter/diluter are set to 70% (70 μL) for the sample syringe and 50% (0.5 mL) for the reagent syringe.

3. Pipette at least 120 μL of sample into the OPTIMATE sample cups.

4. Prime the pipetter/diluter with 200 mM glycine, pH 9 buffer containing 0.05% BSA-pf and 0.1% sodium azide.

5. Start Chemistry #26 - USER CHEMISTRY #26 following all printed instructions. The OPTIMATE then automatically pipettes and dispenses sample and buffer into the reaction cups and reads the absorbance after five minutes.

Calculations

A number of calculations must be performed in order to transform the information provided by the OPTIMATE into a % HbA1c result. 2 1. A latex blank reaction (500 μL latex +35 μL buffer) is included in every assay run. The absorbance of this reaction must be subtracted from every other result. 2. For all blood samples, the contribution of the absorbance of hemoglobin to the reaction is calculated using the information collected from USER CHEMISTRY #26. The absorbance result obtained there is divided by seven to calculate the absorbance of 10 μL of blood. This value is then subtracted from the absorbance result obtained above. 3. In order to calculate a standard curve, a dummy immunoassay is programmed using Immunoassay #37 - Program New Test. The following parameters are programmed as USER IMMUNOASSAY #27.

Protocol - #1
Calibrator Values - enter the assigned calibrator values for the Glc-peptide calibrators (in terms of μM HbA1c). These are dependent on the lot of Ab-latex used. The values of all other parameters are unimportant but must be entered in order to store the calibrator values.

4. A four parameter logit standard curve is generated using Immunoassay #33 - Immunoassay Calculations.

Test #- #27
Calc Scheme - 1. 4 Param Logit
Enter Absorbance results (minus latex blank) for the Glc-peptide calibrators.
The OPTIMATE then generates the standard curve, calculating the standard deviation of the curve and the four parameters. Once completed, calculate HbA1c of the unknown samples by entering the absorbance (— ltx blank, —Hb contrib) for all samples. The result printed is the μM HbA1c concentration.

5. The concentration of hemoglobin in each of the blood samples is calculated using the information from USER CHEMISTRY #26. The concentration of hemoglobin is first calculated in terms of g/dL and then this information is used to determine the mM concentration of hemoglobin β chains present.

$$Hb = (g/dL) = \frac{\text{Abs. from CHEM \#26} \times 16114.5 \times 252}{9.79 \times 1.0 \times 10{,}000}$$

where
16114.5 = MW of one Hb subunit
252 = dilution factor
9.79 = quarter millimolar extinction coefficient
10,000 = correction for unit conversion
Conc of hemoglobin in mM beta subunits:

$$\text{mM beta-Hb Subunits} = \frac{\text{g/dL Hb} \times 10}{64{,}456} \times 1000 \times 2$$

where
10 = conversion factor to g/L
64,456 = MW of hemoglobin (four subunits)
1000 = conversion factor to mM
2 = conversion factor for Hb to beta-Hb 6. Now that the $\mu$M HbA$_{lc}$ concentration and the hemoglobin concentration (both in terms of the beta subunits) are known, the % HbA$_{lc}$ can be determined.

Clinical Study

Figure 3:
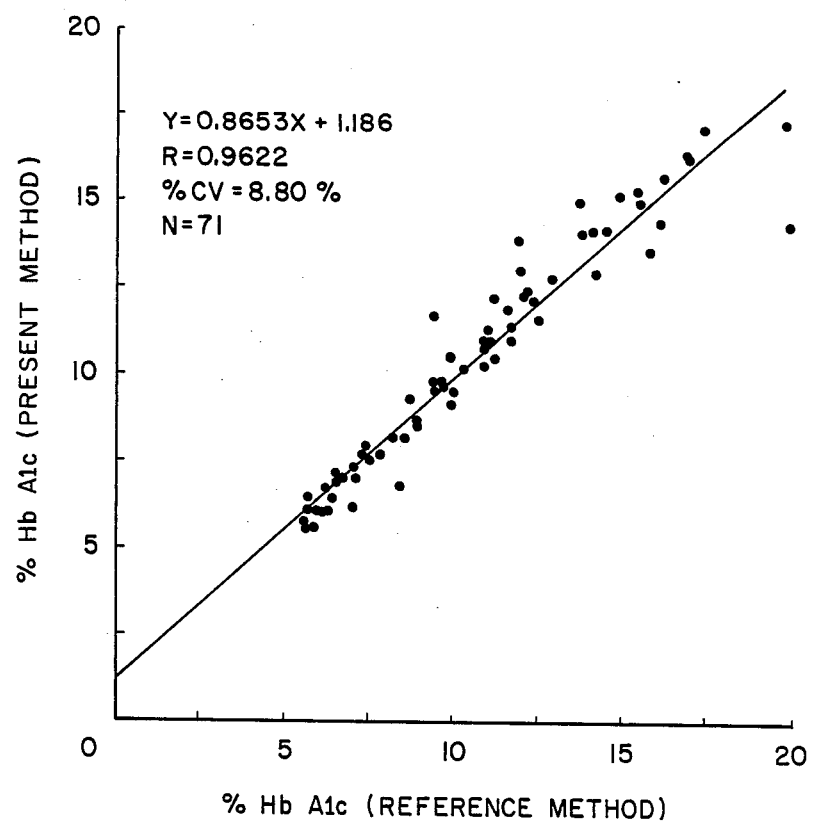

Clinical samples (71) were obtained from a local clinical laboratory which had assayed the samples by the conventional HbA1c affinity chromatography method (Isolab, Akron, OH, U.S.A.). The samples were assayed as above using the present invention. The correlation is presented as FIG. 3 of the drawing.

4. HEMOGLOBIN Ao ASSAY

Figure 4:
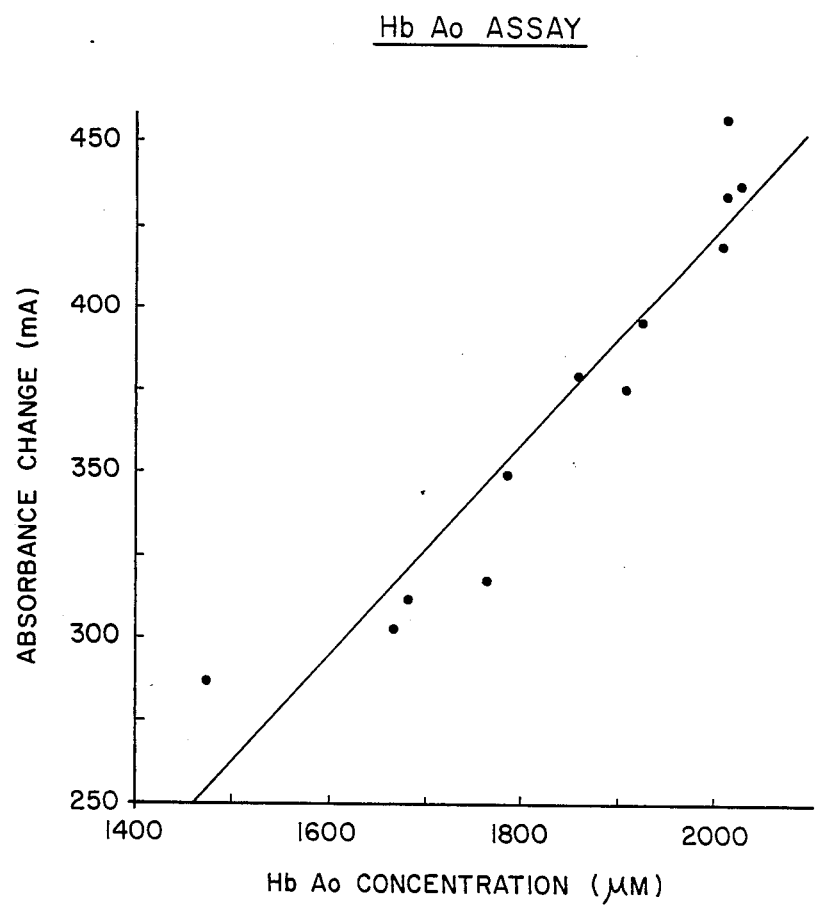

Using a buffer of 50 mM phosphate, pH 7.4, containing 80 mM sodium chloride, 0.05% BSA and 0.02% sodium azide, the % Ao of a sample was determined using the procedure described above for % A1c. A typical dose response curve is shown in FIG. 4 of the drawing.

The present invention has been particularly described and exemplified above. Obviously, many other variations and modifications of the invention can be made without departing from the spirit and scope thereof.

What is claimed is:

1. In an analytical method for determining an analyte in a lysed blood sample by latex agglutination immunoassay, wherein (a) an aqueous reaction mixture is formed by combining the lysed blood sample with a multivalent latex antibody reagent comprising an anti-analyte antibody, or a fragment thereof, bound to a water suspensible latex particle, and additionally when the analyte is monovalent, with an agglutinator reagent comprising a plurality of epitopic binding sites for the anti-analyte antibody or fragment thereof, and (b) the resulting agglutination in the aqueous reaction mixture is measured as a function of analyte in the blood sample, the improvement which comprises forming the aqueous reaction mixture to have a pH of about 8.5 or greater, whereby nonspecific agglutination of the latex reagent due to the presence of hemoglobin in the blood sample is substantially overcome.

2. The method of claim 1 wherein said latex particle has an effective net negative surface charge when suspended in an aqueous solution having a pH of about 7 or below.

3. The method of claim 1 wherein said latex particle is polystyrene.

4. The method of claim 1 wherein the aqueous reaction mixture is formed to have a pH of from about 8.5 up to the pH at which the immunoreactivity between the analyte and the latex reagent is substantially diminished.

5. The method of claim 1 wherein the aqueous reaction mixture is formed to have a pH of between about 8.75 and about 10.

6. The method of claim 1 wherein the aqueous reaction mixture is formed to have a pH of about 9.

7. An analytical method for determining hemoglobin A1c in a test sample comprising blood lysate by particle agglutination inhibition immunoassay, which method comprises the steps of:
(a) forming an aqueous reaction mixture comprising the blood sample and assay reagents comprising (1) a multivalent antibody reagent comprising an antibody, or a fragment thereof, to hemoglobin A1c bound to a water suspensible polystyrene latex particle, and (2) an agglutinator reagent comprising a plurality of glycated peptides corresponding to the glycated peptide sequence of hemoglobin A1c, said reaction mixture formed to have a pH of about 8.5 or greater, and
(b) measuring the resulting agglutination as a function of hemoglobin A1c in the blood sample.

8. The method of claim 7 wherein the pH of the reaction mixture is less than about 10.

9. The method of claim 7 wherein the pH of the reaction mixture is between about 8.75 and about 9.5.

10. The method of claim 7 wherein the pH of the reaction mixture is about 9.

11. The method of claim 7 wherein the blood sample has been pretreated with a hemoglobin denaturant and the antibody reagent comprises a monoclonal antibody, or a fragment thereof, that binds specifically to denatured hemoglobin A1c.

12. A test system for determining an analyte in a blood sample by latex agglutination immunoassay, comprising:
(1) a multivalent latex antibody reagent comprising an anti-analyte antibody, or a fragment thereof, bound to a water suspensible latex particle,
(2) when the analyte is monovalent, an agglutinator reagent comprising a plurality of epitopic binding sites for the anti-analyte antibody or fragment thereof, and
(3) a buffer capable of maintaining the pH of the reaction mixture formed by combination of the test system components with the blood sample at about 8.5 or above.

13. The test system of claim 12 wherein said latex particle has an effective net negative surface charge when suspended in an aqueous solution having a pH of about 7 or below.

14. The test system of claim 12 wherein said latex particle is polystyrene.

15. The test system of claim 12 wherein the aqueous reaction mixture is formed to have a pH of from about 8.5 up to the pH at which the immunoreactivity between the analyte and the latex reagent is substantially diminished.

16. The test system of claim 12 wherein the aqueous reaction mixture is formed to have a pH of between about 8.75 and about 10.

17. The test system of claim 12 wherein the aqueous reaction mixture is formed to have a pH of about 9.

18. The test system of claim 12 wherein the analyte is hemoglobin A1c and the agglutinator reagent comprises a plurality of glycated peptide residues corresponding to the glycated peptide sequence of hemoglobin A1c.

19. The test system of claim 18 wherein the latex particle is polystyrene.

20. The test system of claim 19 wherein the buffer is capable of maintaining the pH of the reaction mixture at between about 8.75 and about 10.

21. The test system of claim 19 wherein the buffer is capable of maintaining the pH of the reaction mixture at about 9.

22. The test system of claim 19 which additionally comprises a hemoglobin denaturant and wherein the antibody reagent comprises a monoclonal antibody, or a fragment thereof, that binds specifically to denatured hemoglobin A1c.

23. An analytical method for determining hemoglobin Ao in a lysed blood sample, comprising the steps of:
   (a) forming an aqueous reaction mixture comprising the lysed blood sample and suspended latex particles and maintaining the pH of the reaction mixture at about 8 or below, and
   (b) measuring the agglutination of said latex particles as a function of hemoglobin Ao in the blood sample.

24. The method of claim 23 wherein said latex particles have an effective net negative surface charge when suspended in an aqueous solution having a pH of about 7 or below.

25. The method of claim 24 wherein said latex particles are made of polystyrene.

26. The method of claim 23 wherein the pH of the reaction mixture is maintained from about 8 down to the pH at which the ability of hemoglobin Ao to agglutinate the polystyrene latex particles is substantially diminished.

27. The method of claim 23 wherein the pH of the reaction mixture is maintained between about 8 and about 4.

28. A test system for determining hemoglobin Ao in a blood sample, comprising:
   (1) latex particles, and
   (2) a buffer capable of maintaining the pH of an aqueous reaction mixture comprising the latex particles and the blood sample at about 8 or below.

29. The test system of claim 28 wherein said latex particles have an effective net negative surface charge when suspended in an aqueous solution having a pH of about 7 or below.

30. The test system of claim 29 wherein said latex particles are made of polystyrene.

31. The test system of claim 28 wherein the buffer is capable of maintaining the pH of the reaction mixture at between about 8 and about 4.

* * * * *